(12) United States Patent
Kawachi et al.

(10) Patent No.: US 6,285,787 B1
(45) Date of Patent: *Sep. 4, 2001

(54) IMAGE PICKUP AND PROCESSING DEVICE AND METHOD THEREOF

(75) Inventors: Masahiro Kawachi, Yawata; Toshimichi Masaki, Takatsuki, both of (JP)

(73) Assignee: Omron Corporation, Kyoto (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/962,036

(22) Filed: Oct. 31, 1997

(30) Foreign Application Priority Data

Oct. 31, 1996 (JP) .................................................. 8-304199
Jul. 1, 1997 (JP) .................................................. 9-188890

(51) Int. Cl.[7] .............................. G06K 9/00; G06K 9/62; G02B 27/40; H04N 1/00

(52) U.S. Cl. ......................... 382/209; 382/112; 382/141; 382/145; 382/151; 382/218; 382/294; 250/201.3; 358/401; 358/406

(58) Field of Search ..................................... 382/145, 147, 382/209, 218, 112, 115, 128, 141, 151, 294; 250/201.3; 358/401, 406, 409

(56) References Cited

U.S. PATENT DOCUMENTS

| | | | |
|---|---|---|---|
| 4,591,918 | 5/1986 | Hisano | 348/343 |
| 4,614,864 | 9/1986 | Wu | 250/201.4 |
| 4,677,286 | 6/1987 | Liu | 250/201.3 |
| 4,725,722 | 2/1988 | Maeda et al. | 356/624 |
| 4,743,771 | 5/1988 | Sacks et al. | 250/560 |
| 4,875,104 | * 10/1989 | Kamon | 358/400 |
| 5,029,222 | * 7/1991 | Yamada et al. | 382/218 |

(List continued on next page.)

FOREIGN PATENT DOCUMENTS

| | | |
|---|---|---|
| 19537376-A1 | 4/1996 | (DE) . |
| 0413817A1 | 2/1991 | (EP) . |
| 0 522 769 A1 | 1/1993 | (EP) . |
| 0 617 545 A1 | 9/1994 | (EP) . |
| 0 751 663 A2 | 1/1997 | (EP) . |
| 0 779 603 A2 | 6/1997 | (EP) . |
| 0840107-A2 | 5/1998 | (EP) . |
| 1048053 | 2/1989 | (JP) . |
| 2190836 | 7/1990 | (JP) . |
| 2300731 | 12/1990 | (JP) . |

(List continued on next page.)

OTHER PUBLICATIONS

European Search Report, Jul. 1, 1999.

* cited by examiner

*Primary Examiner*—Leo Boudreau
*Assistant Examiner*—Daniel G. Mariam
(74) *Attorney, Agent, or Firm*—Dickstein Shapiro Morin & Oshinsky LLP

(57) ABSTRACT

An improved image pickup device or method and an improved image processing device or method which directly projects a region specifying image on an object to specify and focus the object within a predetermined region without employing any image display unit so as to take an image of the object and judge the quality of the taken image. An image pickup device (2) includes an image pickup means (22) for taking an image of an object (1) which is focused through a lens (21), and a projecting means (25) for projecting an image (27p) of a predetermined shape on the object. An image processing device (4) compares the image taken by the image pickup device (2) with a predetermined image stored beforehand to produce a result of such comparison.

15 Claims, 17 Drawing Sheets

U.S. PATENT DOCUMENTS

| | | | |
|---|---|---|---|
| 5,067,162 | * 11/1991 | Driscoll, Jr. et al. | 382/126 |
| 5,220,436 | 6/1993 | Aosaki et al. | 358/401 |
| 5,335,082 | * 8/1994 | Sabie | 347/232 |
| 5,604,344 | * 2/1997 | Finarov | 250/201.3 |
| 5,692,068 | * 11/1997 | Bryenton et al. | 382/135 |
| 5,710,662 | * 1/1998 | Nishida | 250/201.3 |
| 5,790,710 | * 8/1998 | Price et al. | 250/201.3 |
| 5,929,961 | * 7/1999 | Nishi et al. | 349/187 |

FOREIGN PATENT DOCUMENTS

| | | |
|---|---|---|
| 05037845 | 2/1993 | (JP) . |
| 06334905 | 12/1994 | (JP) . |
| 07244318 | 9/1995 | (JP) . |

(a) UNFOCUSED        (b) FOCUSED

IMAGE PICKUP AND PROCESSING DEVICE AND METHOD THEREOF

BACKGROUND OF THE INVENTION

1. Field of the Invention

This invention relates to an image pickup device and method which takes an image of an object in order to inspect or measure the object employing an image processing technique, and to an image processing device and method for judging if the object is good based on the taken image.

2. Discussion of the Related Art

It is well known to employ an image inspection device which takes an image of an object by an image pickup device to execute matching of the taken input image with a model image as a reference for judging based on a result of the matching whether or not the object is good. FIG. 19 shows a block diagram of such a conventional image inspection device in which a camera 71 takes an image of an object 70 and the taken input image is displayed on a monitor screen 73a of an image display device 73. On setting the device, an operator adjusts the position relation of the object 70 and the camera 71 by watching the image display device 73 so that the input image 70p of the object 70 comes within the range of the monitor screen 73a, or by visually observing the blurriness of the input image 70p so that it may be focused.

The operator simultaneously watches the input image 70p and a region designation image 72p of a frame shape produced from the controller 72 which are displayed on the monitor screen 73a so that the region designation image 72p is overlapped with the input image 70p by operating a manipulator 74 for specifying a detection object region.

In such a conventional image inspection device, the input picture 70p of the object 70 and the region designating image 72p have to be displayed on the monitor image 73a of the image display device 73, whereby there are required an image output function and a graphic process function or the like resulting into an expensive system.

A position of the camera 71 has to be adjusted by an operator confirming the focus of the input image 70p with the monitor screen 73a for a focus adjustment. Accordingly, the focus adjustment is difficult when the installation position of the camera 71 is far from the installation position of the image display device 73.

SUMMARY OF THE INVENTION

It is, therefore, a primary object of this invention to provide an improved image pickup device or method and an improved image processing device or method which directly projects a region designating image on an object to specify and focus a predetermined region without employing any image display unit so as to take an image of the object and judge the quality of the taken image.

According to a first aspect of this invention, there is provided an image pickup device which includes an image pickup means taking an image of an object which is focused through a lens, and a projecting means for projecting an image of a predetermined shape on the object. In this device, a region designating image may be directly projected on the object by the projecting means, and positional and focal adjustment for a predetermined region may be executed by visually watching the projected image without employing any image display device.

According to a second aspect of this invention, there is provided an image pickup device which includes an image pickup means taking an image of an object which is focused through a lens, a projecting means for projecting an image of a predetermined shape on the object, and an illumination means disposed around the lens for illuminating the object. In this device, a region designating image may be directly projected on the object by the projecting means, the projected image may be visually watched illuminating a predetermined region of the object by the illumination means, and positional and focal adjustment for the predetermined region may be executed without employing any image display device.

According to a third aspect of this invention, there is provided an image processing device which processes an image taken by an image pickup device, including an image pickup means taking n image of an object which is focused through a lens and a projecting means for projecting an image of a predetermined shape on the object, to be compared with a predetermined reference or a predetermined image stored beforehand to produce its comparison result. This device may allow the judgment of the quality of the object without employing any image display device.

According to a fourth aspect of this invention, there is provided an image pickup method for projecting an image of a predetermined shape from an image pickup device, and focusing an image on an object surface at a predetermined remote position from the object to take an image of the object. In this method, positional and focal adjustment of a predetermined area may be executed by visually watching the projected image without employing any image display device.

According to a fifth aspect of this invention, there is provided an image pickup method for projecting an image of a predetermined shape from an image pickup device, and focusing an image on a surface of an object at a predetermined remote position from the object, taking an image of the object, processing the taken image to be compared with a predetermined reference or a predetermined image stored beforehand, and producing its comparison result. In this method, the quality of the object may be judged without employing any image display device.

According to a sixth aspect of this invention, there is provided an image pickup device including an image pickup mean: taking an image of an object which is focused through a lens, a projecting means for projecting an image of a predetermined shape on the object, and an illumination means around the lens for illuminating the object, in which all of the means are enclosed in a housing and respectively fixed at their positions within the housing. In this device, a region designating image may be directly projected on the object by the projecting means, and positional and focal adjustment for a predetermined region may be executed by visually watching the projected image without employing any image display device.

According to a seventh aspect of this invention, there is provided an image processing device which includes an A/D converter for converting an output from an image pickup device into a digital signal, an image processing unit for image processing the digitized signal, and an output unit for producing a result of the picture processing, which are respectively enclosed within a housing. In this device, the quality of the object may be judged without employing any image display device.

BRIEF DESCRIPTION OF THE DRAWINGS

Other objectives and advantages of this invention will be more readily apparent from the following detailed description provided in conjunction with the following figures, of which.

DETAILED DESCRIPTION OF THE INVENTION

Figure 1:
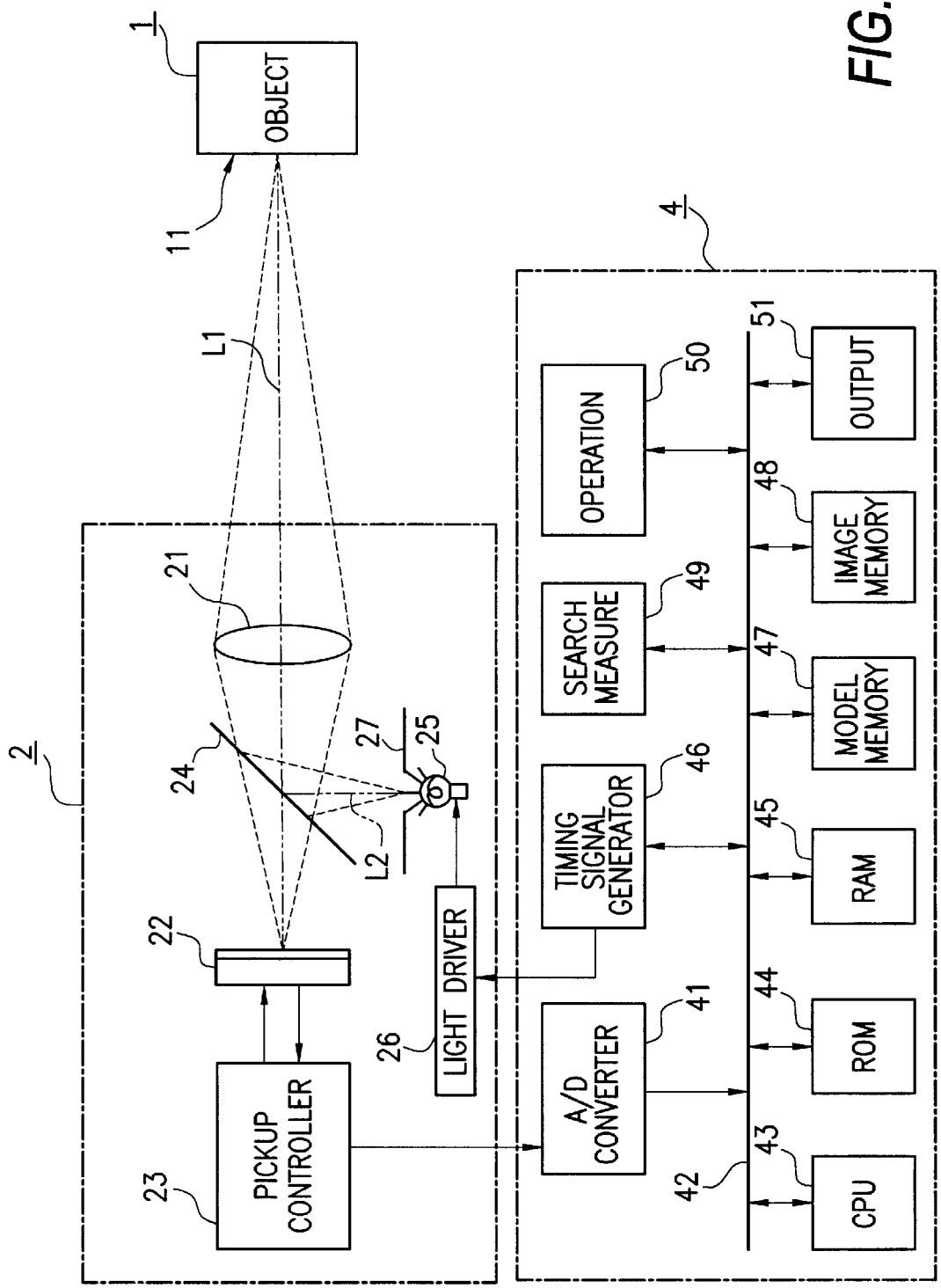
FIG. 1 is a block diagram of an image pickup device and an age processing device as a first embodiment of this invention.

Referring, now, to FIG. 1, there is shown a block diagram of an image pickup device 2 and an image processing device 4 as a first embodiment of this invention, in which an image of an object 1 to be inspected or measured is taken by the image pickup device 2 to generate a picture signal and the object 1 is inspected by the image processing device 4 employing a digital image processing technique based on the generated picture signal. The devices 2 and 4 are respectively enclosed by separate housings. The image pickup device 2 is placed on a line passed by the object 1, for instance, for 50 cm intervals, and the image processing device 4 is placed away from the image pickup device 2 and connected through a cable.

The image pickup device 2 includes an image pickup element 22 (for example, a two-dimensional CCD image pickup device) which is disposed at a position to which an image of the object 1 is focused through a lens 21, an image pickup controller 23 converting the image pickup signal obtained by drive-controlling the element 22 for photoelectric conversion into a picture signal, and a half mirror 24 serving as a half transmission mirror disposed between the lens 21 and the element 22. The half mirror may be replaced with a dichroic mirror as the half transmission mirror, it desired. Because the half mirror transmits a part of incident light and reflects the remainder, both the transmitted light quantity and the reflected light quantity are reduced. The dichroic mirror, however, selectively reflects a part of the incident light at a visible light area and transmits the reminder by using an optical interference, so that reduction of a quantity of projection light by a projection light source 25 and a quantity of received light by the image pickup element 22 can be minimized.

The half mirror 24 is placed at a predetermined angle (45 degrees in this embodiment) on an optical axis L1 extending to the object 1 and the image pick up element 22. The mirror reflects to the lens 21 a part of light projected from the light source 25 (such as a light emitting diode) placed on an optical axis L2 crossing the optical axis L1 (at 90 degrees in this embodiment), and transmits a part of the light transmitted from the lens 21 to be focused on the image pickup element 22. The light source 25 is flash-driven by a drive signal produced from a light source driver 26.

A slit plate 27 provided with a plurality of slits is so disposed in front of the light source 25 that the distance from the plate 27 to the mirror 24 on the optical axis L2 is the same as that from the mirror 24 to the element 22 on the optical axis L1. Accordingly, a shape of slits on the slit plate 27 is projected and focused on a surface (measurement surface) 11 of the object 1. The slits of the slit plate 27 will be described later in detail referring to FIG. 2. Thus, a projection means is composed by the projection light source 25 and the slit plate 27.

The image processing device 4 includes an analog/digital (A/D) converter 41 for converting the picture signal produced from the image pickup device 2 into a digital image signal, and the A/D converter 41 is connected with a system bus 42.

The system bus 42 is provided with a CPU 43 for controlling the whole device, a read only memory (ROM) 44 for storing program data for operating the CPU 43 and various data, a read/write random access memory (RAM) 45 temporarily storing processed data, a timing signal generator 46 controlling the light source driver 26, a model memory 47 storing a model image representing a reference, an image memory 48 storing input image, a search measure unit 49 comparing the input image with the model image, an operation unit 50 instructing registration of the model image and the inspection and measurement of the object 1, and an output unit 51 producing a judgment result about the quality of the object 1.

Figure 2:
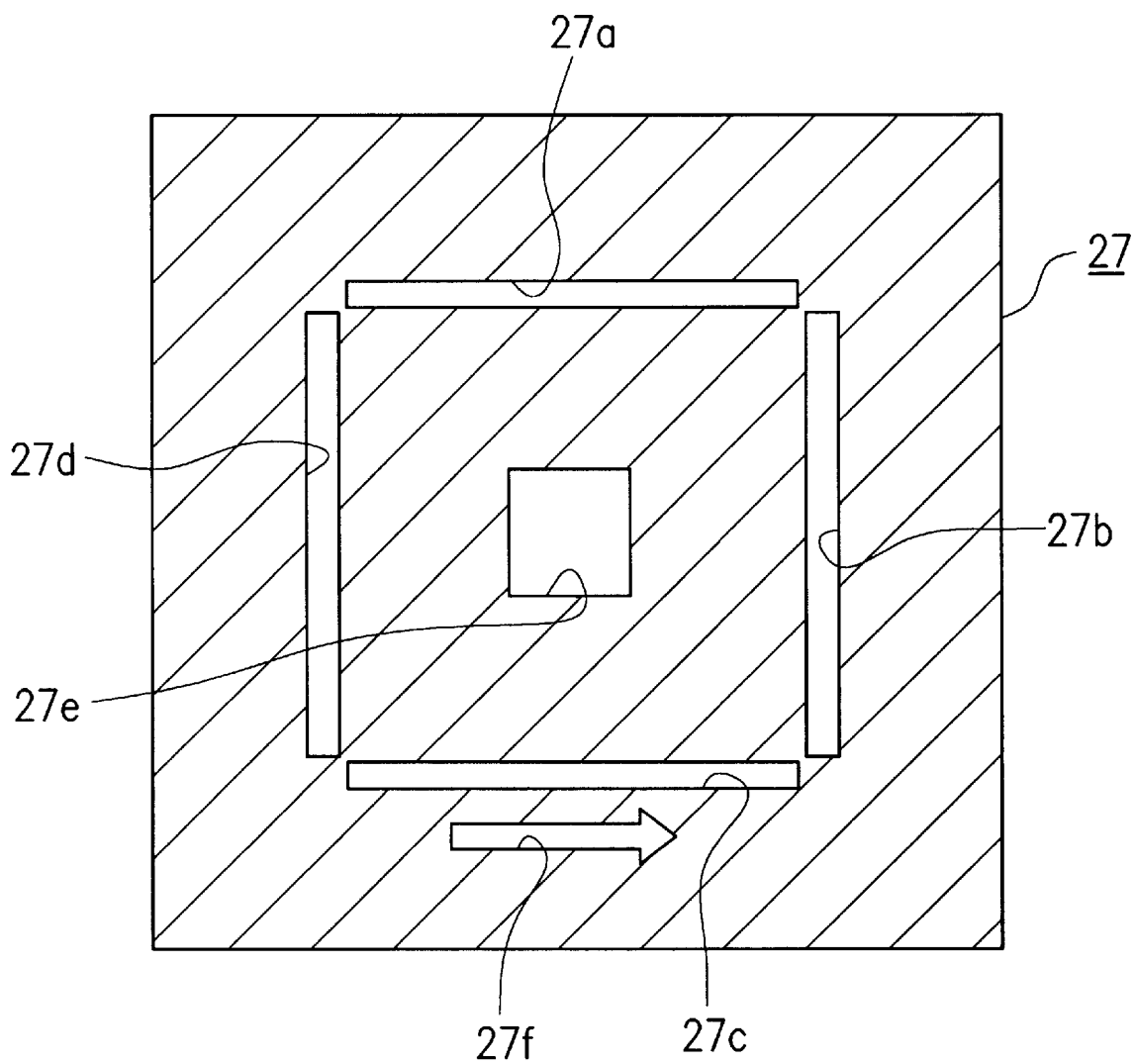
FIG. 2 shows a construction of a slit plate.

In FIG. 2, there is shown a construction of the slit plate 27 provided with the plurality of slits 27a through 27f disposed on a flat plate blocking light so as to transmit light therethrough, in which four slits 27a through 27d of a thin belt shape are disposed for projecting a measuring area of a foursquare frame on the object 1 and the slit 27e of foursquare is disposed at a center to project a registration area for registering a model image.

The slit 27f of an arrow mark shape disposed outside and in parallel with the slit 27c for forming measuring area is disposed to project a flow direction of the line where the object for image pickup moves, so that an operator may set the image pickup device 2 in a correct direction watching the arrow mark image projected by the slit 27f.

Figure 3:
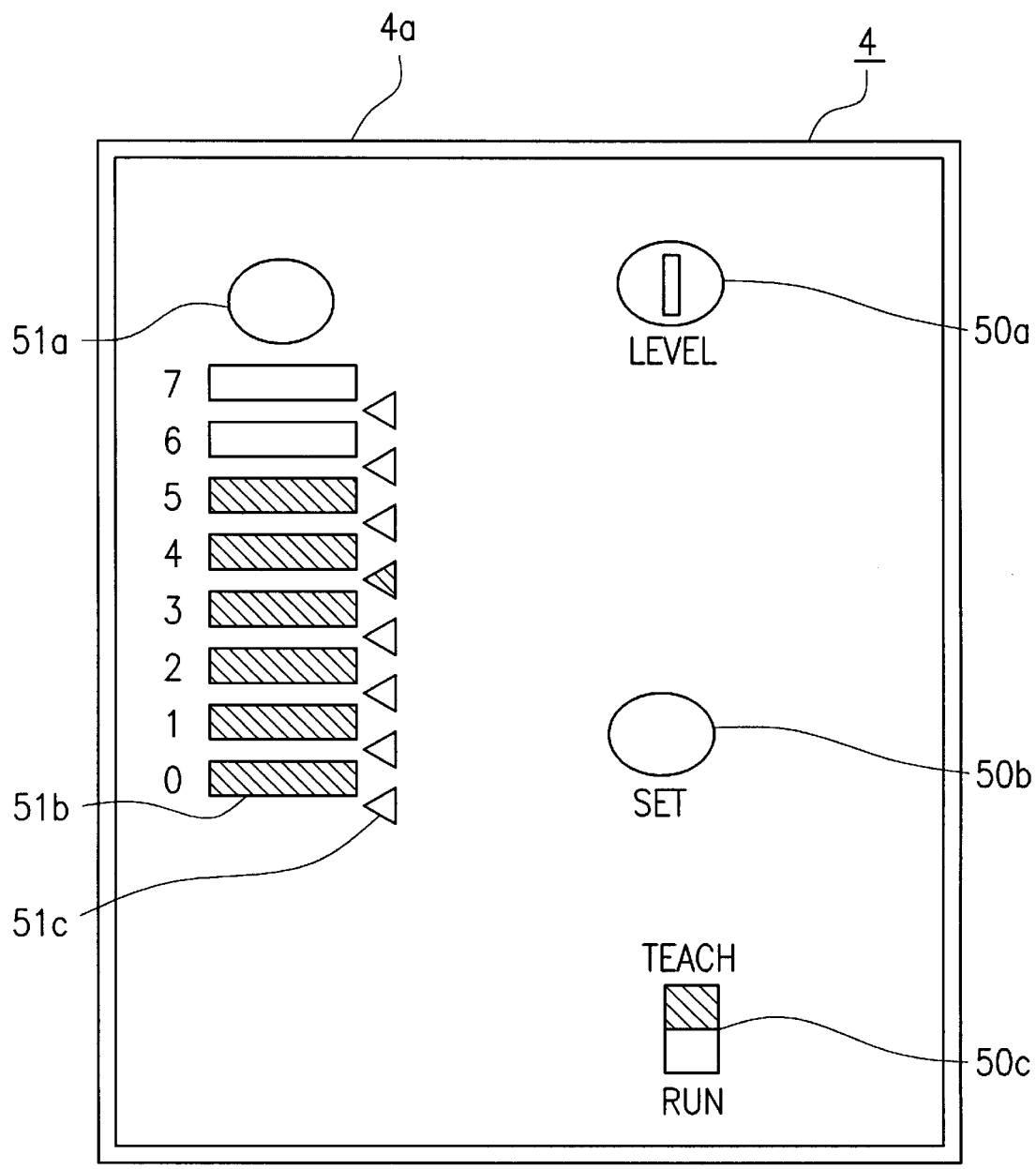
FIG. 3 is a plane view of a panel of a housing of the image processing device.

FIG. 3 is en exile of a top view of a panel of a housing 4a of the image processing device 4 which includes the operation unit (50) having various manipulators 50a to 50c and the output unit (51) having various display as 51a to 51c. An operation display lamp 51a is represented by a LED (light emitting diode) which turns on when a result of inspection of the object 1 is ready for output but turns off unless so. A level display lamp 51b is a series of LEDs which display a consistent degree between an input image of the object 1 and a model image in eight steps 0 to 7. In this embodiment, LEDs 0 to 5 are turned on whereby the consistent degree is indicated as 5. A threshold lamp 51c is a series of LEDs which display eight steps 0 to 7 about a threshold value judging the quality of the object 1. In this embodiment, an LED between 3 and 4 is turned on which means a threshold is placed therebetween. A threshold value trimmer 50a is a rotary manipulator for setting a threshold value to judge the quality of the object 1- A teach button 50b is a switch manipulator to be depressed when a model image is registered. An operation mode selecting switch 50c is a slide manipulator to select one of a TEACH mode to register a model image and a RUN mode to inspect and measure the object 1 transmitted on the line.

Figure 4:
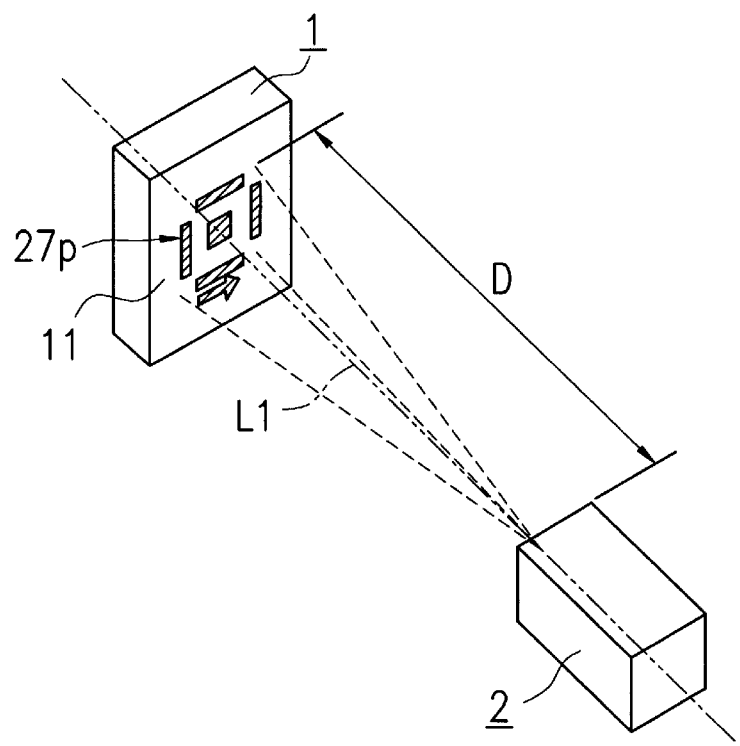
FIG. 4 is a perspective view of the image pickup device and an object to show a positional relation therebetween.

On setting thus constructed devices, as shown in FIG. 4, the image pickup device 2 is placed at a predetermined distance D from the object 1 to adjust the position of the device 2 so that a region designating image 27p projected by the slits 27a to 27f of the slit plate 27 may be focused on a predetermined position of a measurement surface 11 of the object 1, wherein the image pickup device 2 is so disposed that the optical axis L1 is perpendicular to the measurement surface 11 of the object 1 and the distance D is defined by a focal distance of the lens 21.

Figure 5:
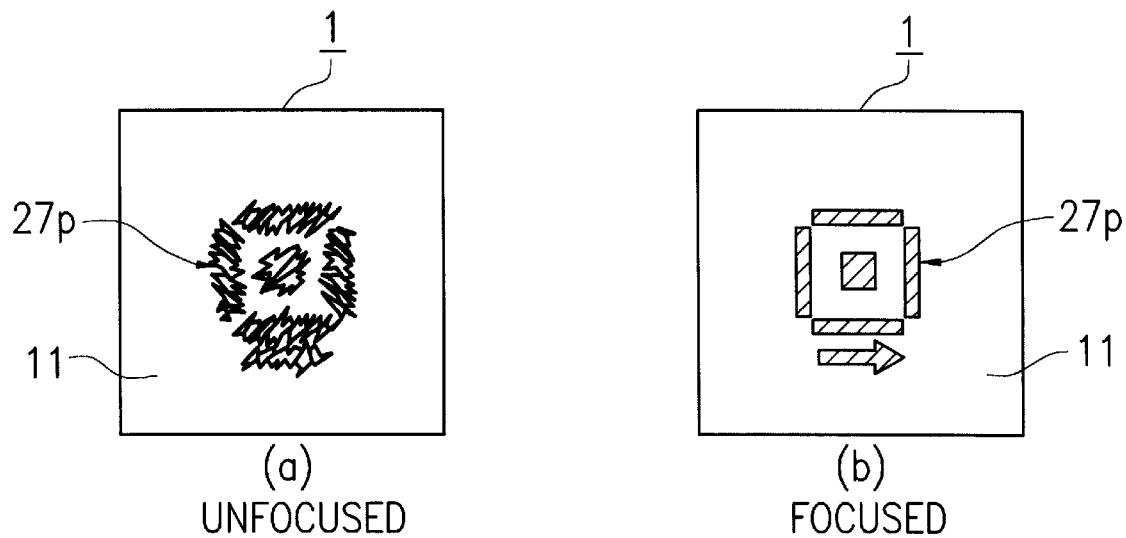
FIG. 5 shows an image projected on the object.

The operator observes the blur condition of the region designating image 27p focused on the object 1 by visual inspection, adjusts the distance D when the contour is blurry for a focus adjustment to obtain a sharp contour of the image as shown in FIG. 5.

Figure 6:
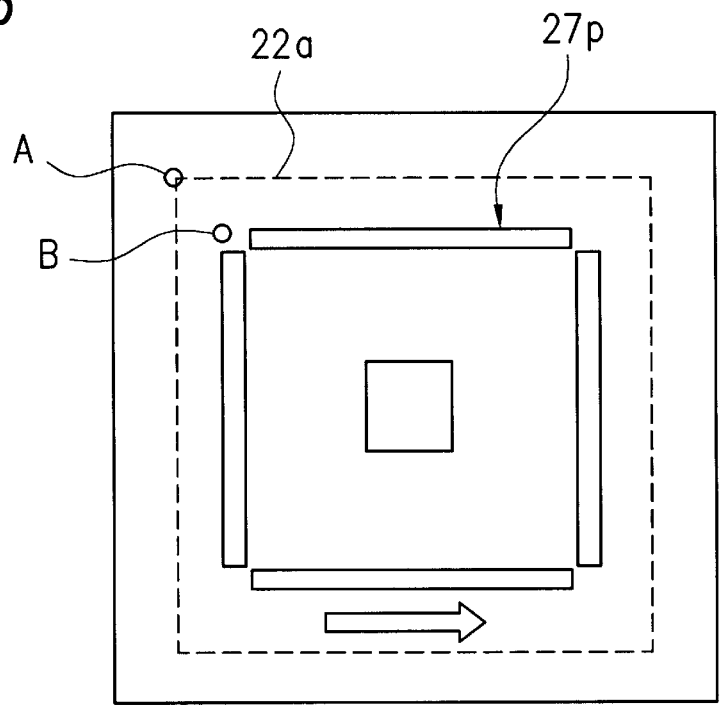
FIG. 6 shows a status in which an image pickup region of an image pickup element coincides with a region designating image projected on the object.

Upon completion of such focus adjustment, the operator executes a recognition process to recognize a position relation between the pickup region of the image pickup element 22 and the region designating image 27p projected on the measured surface 1a of the object 1. As shown in FIG. 6, it is desirable that both center positions of the image pickup region 22a of the image pickup element 22 shown in broken lines and the region designating image 27p agree. For this purpose, however, extremely high accuracy is demanded to position the image pickup element 22 and the slit plate 27.

Figure 7:
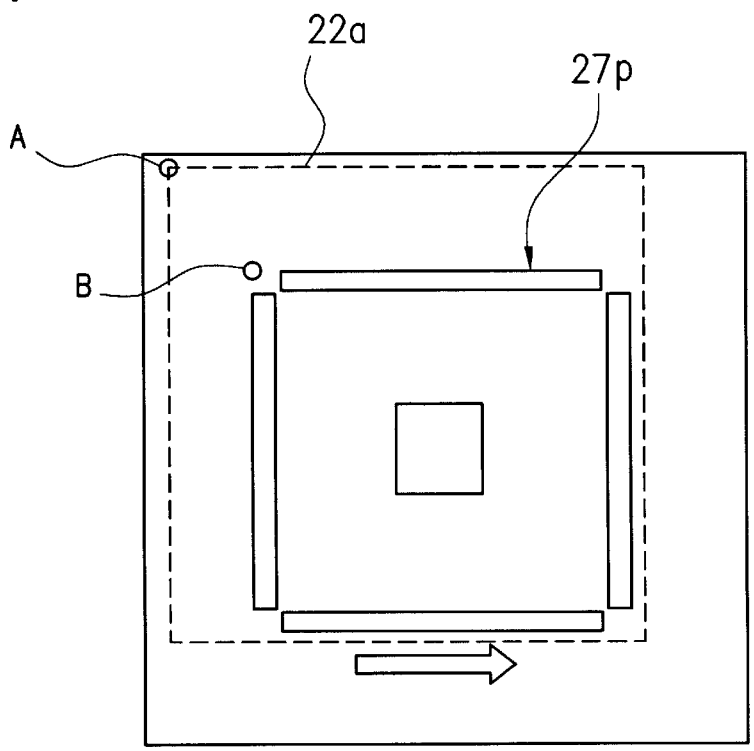
FIG. 7 shows a status in which an image pickup region of the image pickup element is offset from a region designating image projected on the object.

For precise image processing when the accuracy for positioning the image pickup element 22 and the slit plate 27 is rough and the image pickup region 22a somewhat deviates from the region designating image 27p about their positions as shown in FIG. 7, the position relationship between the image pickup region 22a and the region designating Image 27p is recognized beforehand so that the position of the region designating image 27p may be specified into a position within the image pickup region 22a.

Recognition of predetermined coordinates of the image pickup region 22a and the region designating image 27p, for example, the coordinates of points A and B on left top, allows the position relationship between the image pickup region 22a and the region designating image 27p to be recognized. As another method for recognizing the position relationship of the both, white paper is placed on the measurement surface 11 of the object 1 and the region designating image 27p is projected on the white paper to be taken by the image pickup element 22. When the half mirror 24 is replaced with a dichroic mirror to stop the transmission of light of the region designating image 27p, a sheet of paper depicted by a pattern having the same size as that of the region designating image 27p may be put together with the measurement surface 11 of the object 1 and the region designating image 27p may be projected on the white paper to be taken by the image pickup element 22.

Next, the operator registers a model image representing a reference. This registration process is done by the image pickup element 22 which takes an image of a pattern within a registration region image 27q projected on the measurement surface 11 of the object 1 by the slit 27e of the slit plate 27, and by storing the taken pattern as a model image in-the model memory 47 of the image processing device 4. This process is performed by actuating the operation mode selecting switch 50c of the operation unit 50 into a side "TEACH" and depressing the teach button 50b.

The image pickup device 2 takes an image of the object by the image pickup element 22 to convert the taken pickup signal into a picture signal by the image pickup controller 23 for application to the image processing device 4 which converts the picture signal into a digital image signal by the A/D convertor 41 to be stored into the image memory 48. The CPU 43 finds a position for the registration region image 27q in view of the previously obtained position relationship of the image pickup region 22a and the region designating image 27p, and reads an image at the found position from the image memory 48 to be stored into the model memory 47. Thus stored image is the model image.

Upon the completion of adjustment of the position relationship between the object 1 and the image pickup device 2 and the registration of the model image, the operator actuates the line, turns the operation mode selecting switch 50c of the operation unit 50 to a RUN mode to initiate measurement and inspection of the object 1 conveyed on the line.

That is, the image pickup element 22 takes an image of a predetermined position of the measurement surface 11 of the object 1 every time the object 1 comes, and produces the taken image pickup signal to the image pickup controller 23 which converts the pickup signal into a picture signal to be applied to the image processing device 4.

In the image processing device 4, the picture signal is converted into a digital image signal by the A/D converter 41 to be stored into the image memory 48. The CPU 43 finds a position of a measurement region image 27r projected by the slits 27a to 27d of the slit plate 27 based on the previously obtained position relationship of the image pickup region 22a and the region designating image 27p, reads an image at the position from the image memory 48, conducts a gray search at the search measure unit 49 based on the model image stored in the model memory 47 to judge whether the object is good or bad. A result of the judgement is displayed in eight steps by the level display lamp 51b of the output unit 51.

The gray search executes a process in which image data is handled as shading data of several bits without binary encoding and registration image and input image are recognized to agree when a correlation value by doing matching of the registration and input data is larger than a threshold value. Generally, registration image is smaller than the input image, so that the registration image is successively shifted by one pixel for the input image to be compared with the same from end to end thereof to find an agreement point.

Figure 8:
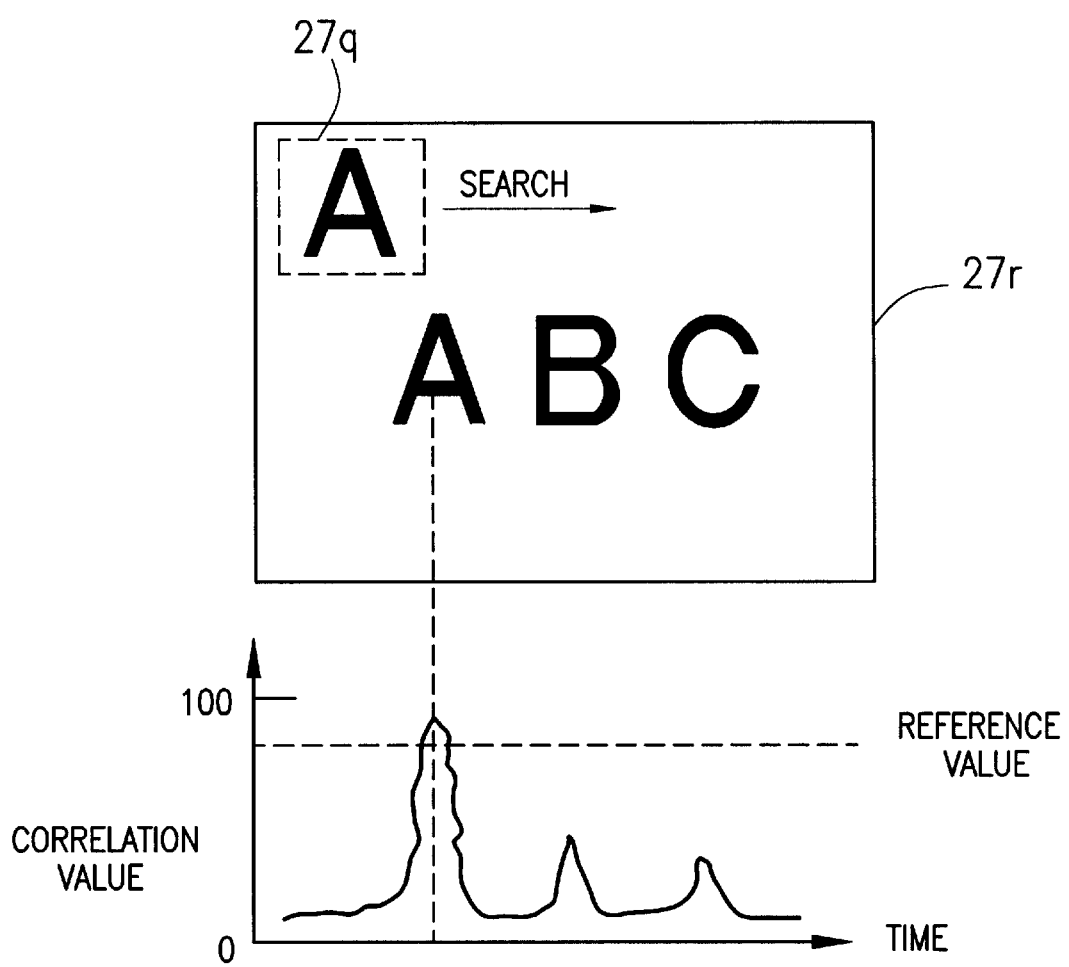
FIG. 8 shows a status in which a measurement region image is searched by a model image.

This process is shown in FIG. 8 in which a measurement region image 27r containing by letters A, B, and C is searched by a region designating image (model image) 27q of the letter A from left top to right bottom. The same image as the model image, viz. the image of the alphabet A, is found at the position where the correlation value of both images exceeds a reference value.

The search process in the search measure unit 49 may employ a binary encoding search instead of the gray search, if desired, in which the image data is binary-encoded with a reference shading level to be compared with a reference area value by measuring the area for judging the quality.

The gray search has advantages. Precise detection can be performed by estimation even if any positional shift smaller than a pixel unit is produced between the registration image and the input image. When some brightness change happens between the registration image and the input image, the comparison about their shape takes a priority to provide almost same result as that of a comparison when both images have the same brightness.

Figure 9:
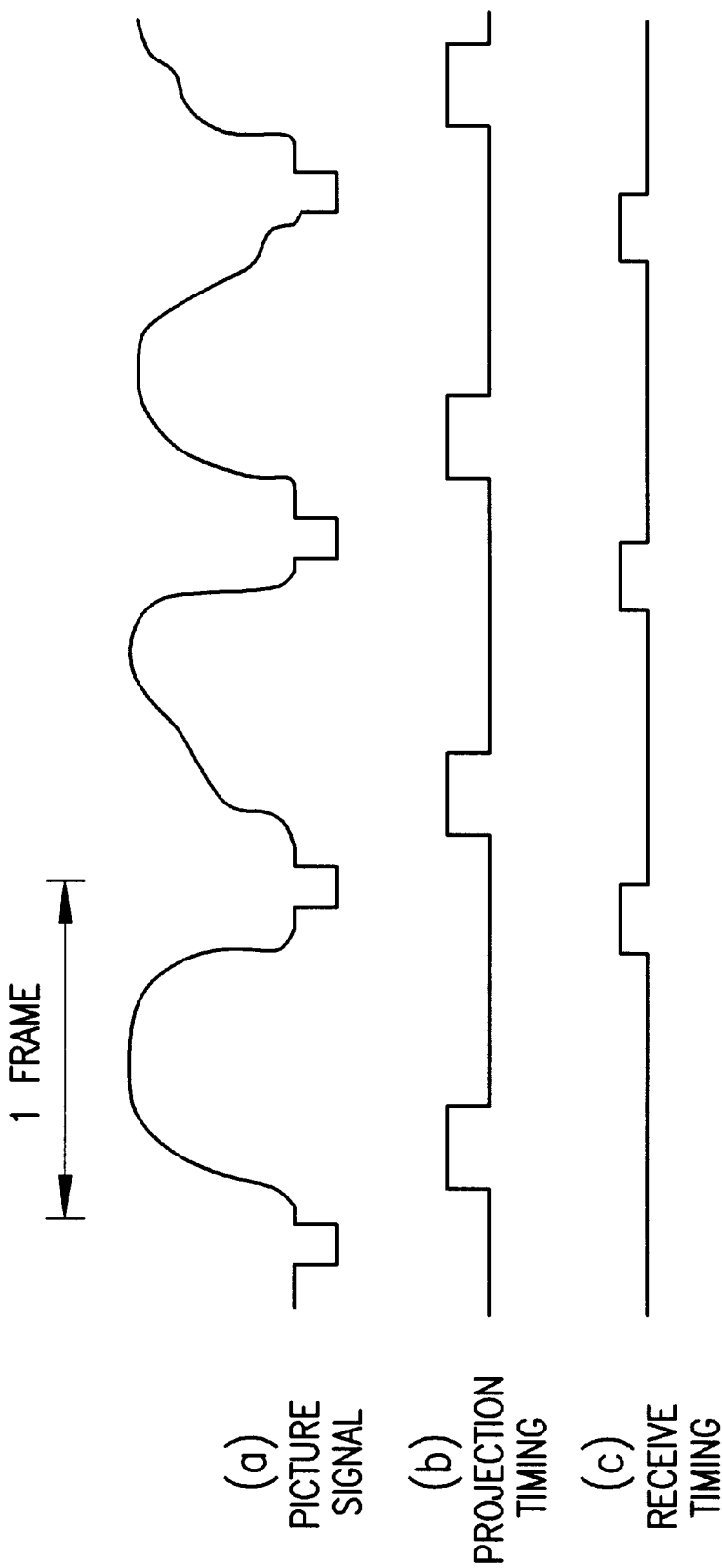
FIG. 9 is a timing chart of (a) a picture signal, (b) a projection timing of a light source, and (c) a light receiving timing by an image pickup element.

FIG. 9 shows wave forms representing a picture signal (a) of one frame of video screen (1 horizontal period: 16.7 msec) produced from the image pickup controller 23, a projection timing (b) of a projection light source 25 for the picture signal (a), and a light receive timing (c) by the image pickup element 22. The projection timing is set to several milliseconds when one horizontal period starts, and the light receive timing is set to several milliseconds when one horizontal period ends. The setting of the timing is fixed.

Thus, the image pickup element 22 is protected from affection by light from the projection light source 25 by shifting the light receive timing of the element 22 from the projection timing of the light source 25. The projection light source 25 visually looks like always lighting by synchronous lighting.

Now, the light receive timing of the image pickup element 22 will be described hereinafter. Generally, an image pickup element is composed of a photoelectric sensor, a shift register and so forth which are disposed on a semiconductor substrate, and has characteristics such that it stores signal charges which are photo-electric translated by the photoelectric sensor when a substrate voltage is a normal voltage but discharges the stored signal charges toward the external without shifting to the shift register when the substrate voltage is higher than the normal voltage.

In view of such characteristics, the substrate voltage is instantly raised to a high voltage each horizontal period to discharge the signal charges having been stored in the photoelectric sensor. The light receive timing is fixed by retaining the substrate voltage at a normal voltage for a predetermined period before end of one frame of video screen and by transferring only the signal charges of light received from the time when the base voltage finally becomes a high voltage to the time when the signal charges are transferred to the shift register.

Figure 10:
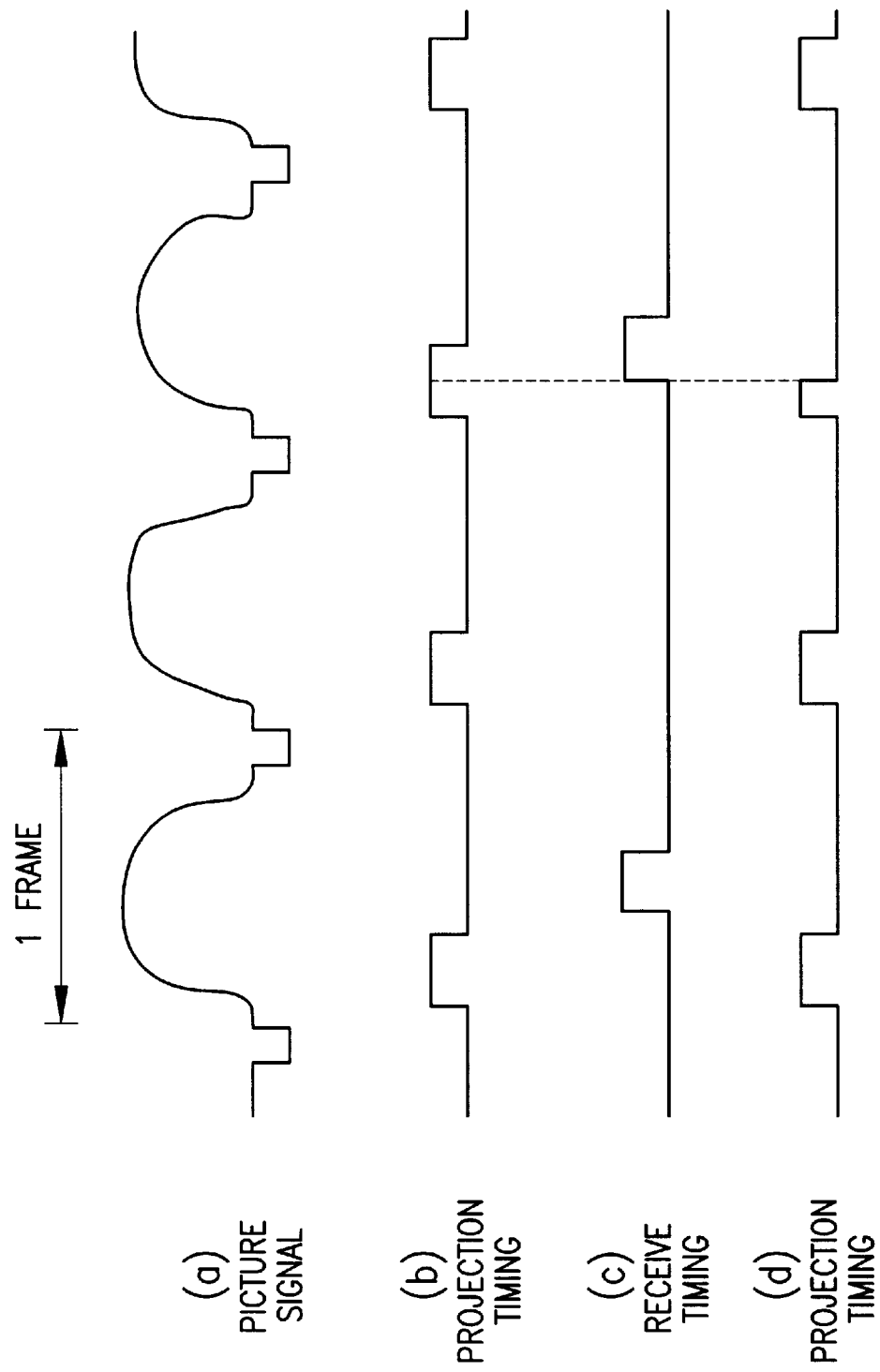
FIG. 10 is a timing chart of (a) a picture signal, (b) a projection timing of a light source, (c) a light receiving timing by an image pickup element externally and irregularly entered by light, and (d) a light projection timing giving a priority to the light receiving timing.

FIG. 10 shows wave forms when a light receive timing (c) of the image pickup 22 irregularly comes. A projection timing (b) of the projection light source 25 for a picture signal (a) is fixed at the start of one horizontal period, and stops the projection of the light source 25 to provide priority to the light receive timing (c) when it is overlapped with the light receive taming (c) to control a light projection timing (d).

In this case also, the image pickup element 22 is protected from affection by light from the projection light source 25 which visually looks like always lighting by synchronous lighting.

(Second Embodiment)

Figure 11:
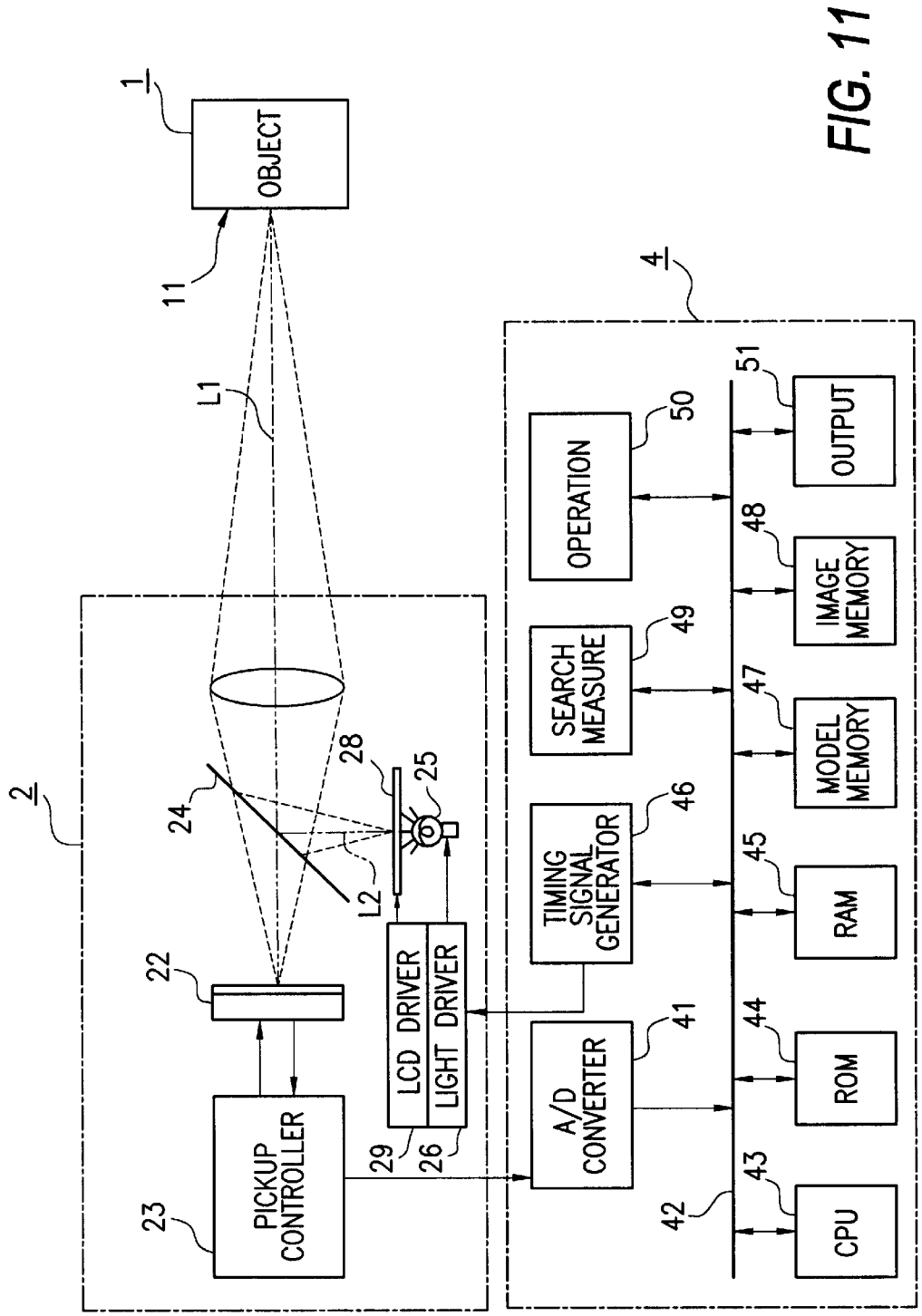
FIG. 11 is a block diagram of an image pickup device and an image processing device as a second embodiment of this invention.

In FIG. 11 there is shown a block diagram of an image pickup device 2 and an image processing device 4 as a second embodiment of this invention, in which the same reference numbers are given to the components corresponding to those of the first embodiment (shown in FIG. 1) and their detailed explanation is omitted.

An image pickup device 2 of this embodiment is provided with a liquid crystal slit plate 28 instead of the slit plate 27 of the first embodiment, and a liquid crystal display driver 29 driving the plate 28. Accordingly, the timing signal generator 46 of the image processing device 4 is designed to have a function controlling the liquid crystal driver 29. Other construction is the same as that of the first embodiment (FIG. 1).

The liquid crystal slit plate 28 is composed of a plurality of liquid crystal cells each of which changes its light transmissivity by an applied voltage. Thus, a projection image of a desired shape is produced by selecting the driven liquid crystal cells by the timing signal generator 46. For instance, it is possible that only the registration region image 27q is projected when a model image is registered, and only the measurement region image 27r is projected when the object 1 is measured and inspected.

(Third Embodiment)

Figure 12:
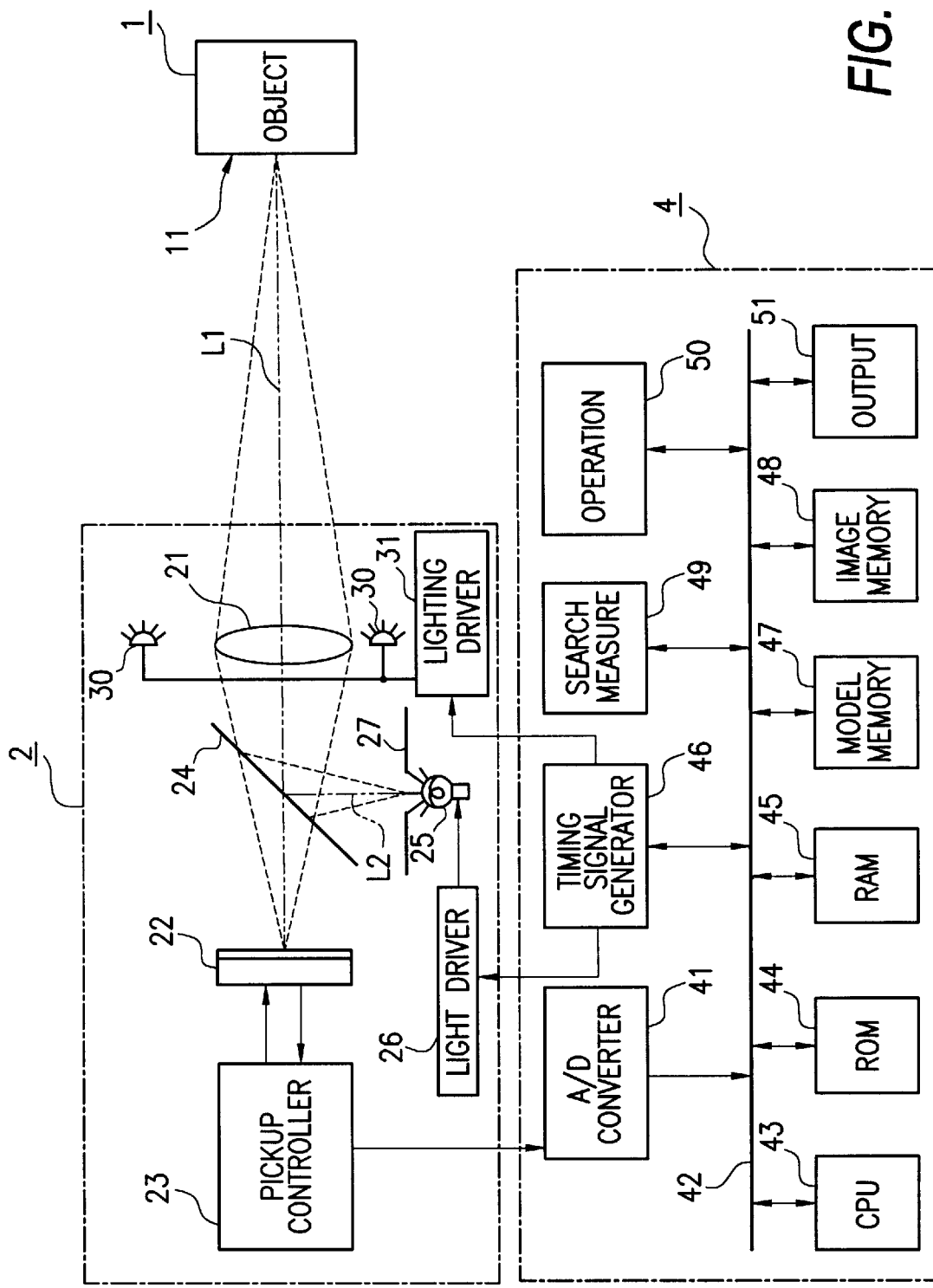
FIG. 12 is a block diagram of an image pickup device and an image processing device as a third embodiment of this invention.

In FIG. 12 there is shown a block diagram of an image pickup device 2 and an image processing device 4 as a third embodiment of this invention, in which the same reference numbers are given to the components corresponding to those of the first embodiment (shown in FIG. 1) and their detailed explanation is omitted. In this embodiment, a plurality of illumination light sources 30 such as LEDs are provided around the lens 21 to light a measurement surface 11 of the object 1. In this embodiment, an image pickup device 2 of this embodiment is provided with a lighting driver 31 for driving the light sources 30, and the timing signal generator 46 of the image processing device 4 is designed to have a function to control the lighting driver 31. Other construction is the same as that of the first embodiment (FIG. 1).

Figure 13:
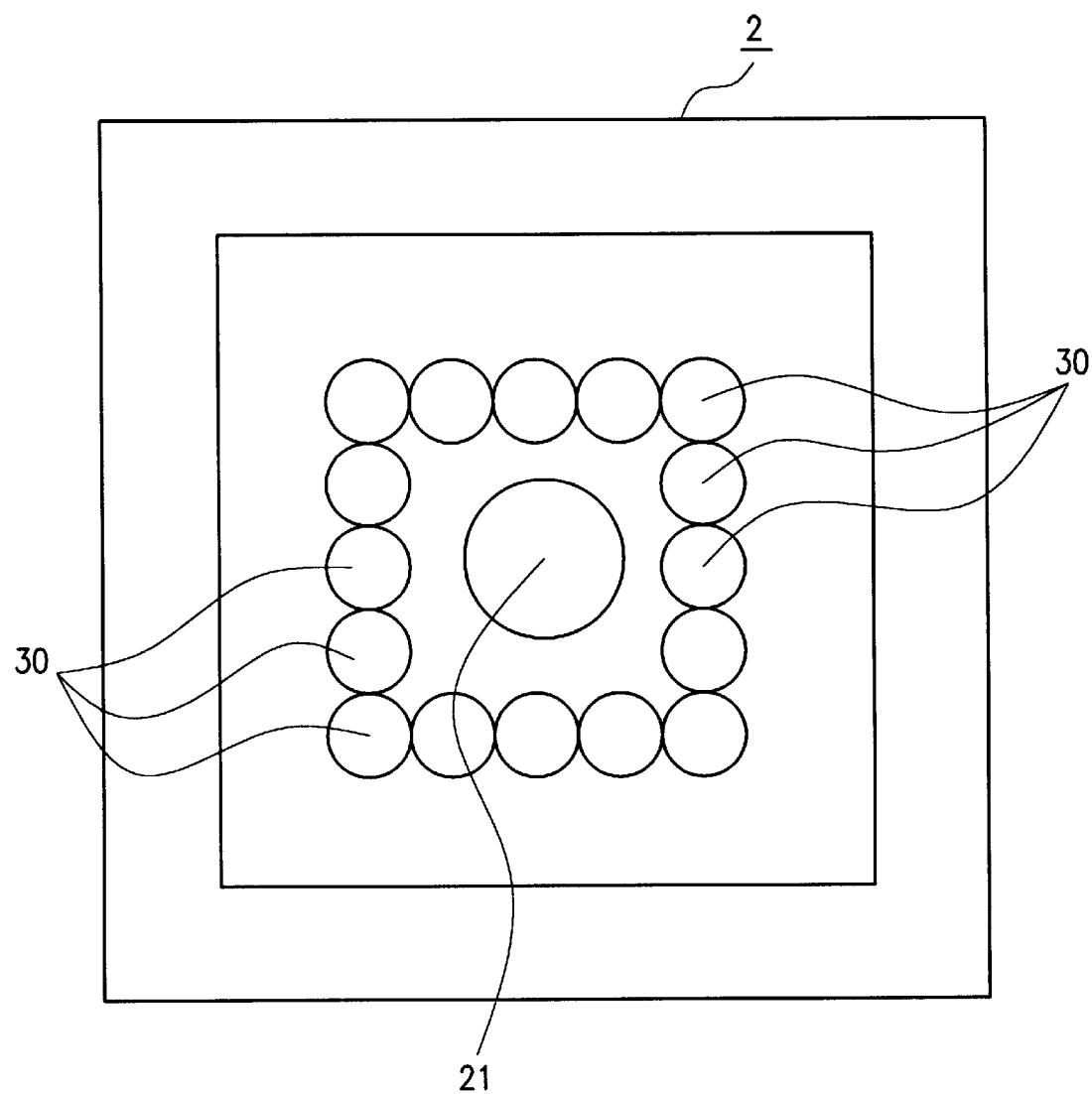
FIG. 13 is a front view of the image pickup device showing position relation of a lens and an illumination light source.

FIG. 13 is a front view of the image pickup device 2 showing a positional relation of the lens 21 and the plurality of light sources 30 arranged in a periphery of the lens 21 in which sixteen illumination light sources 30, viz. five sources in each horizontal direction and each vertical direction respectively. Thus construction provides a sufficient brilliance.

Figure 14:
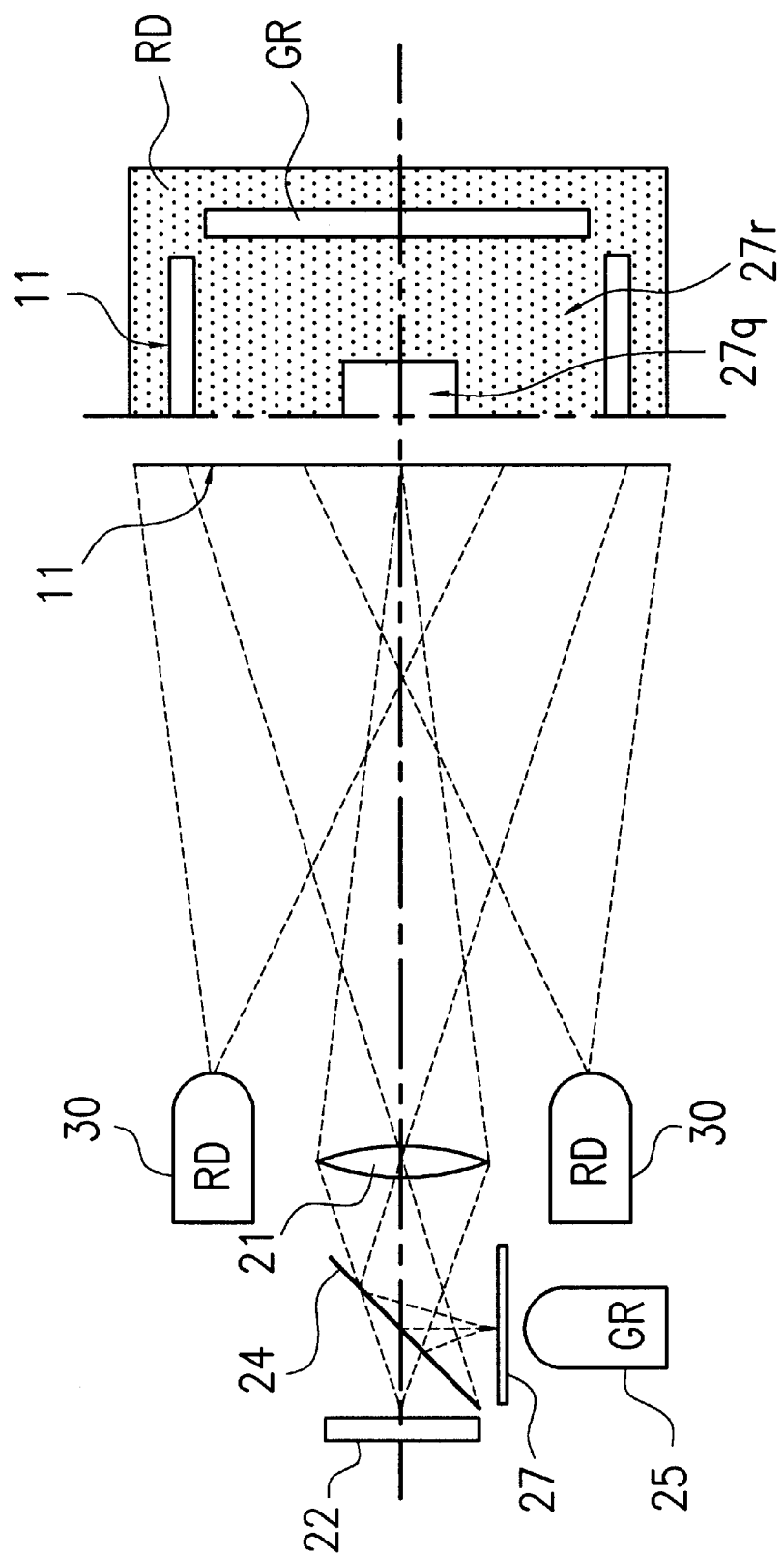
FIG. 14 shows that a measured surface of an object is radiated by light in which a projection light color of a projection light source is different from an illumination light color of an illumination light source.

As shown in FIG. 14, the measurement surface 11 of the object 1 may be radiated by a red illumination color (RD) and the region designating image 27p may be projected by a green color (GD), by changing the projection color of the projection light source 25 from the illumination color of the illumination light sources 30, for instance, setting the luminescence frequency of the sources 25 into a green region (GR) and the luminescence frequency of the sources 30 into a red region (RD). According to this embodiment, if stroboscope luminescence is done with agreement between the light projection ting of the illumination light sources 30 and the light receive timing of the image pickup element 22 to execute the shifting control of projection timing of the projection light source 25 from the light receive timing of the image pickup element 22 as shown in FIGS. 9 and 10, whereby the image pickup element 22 is improved to be protected from affection by external light.

(Fourth Embodiment)

Figure 15:
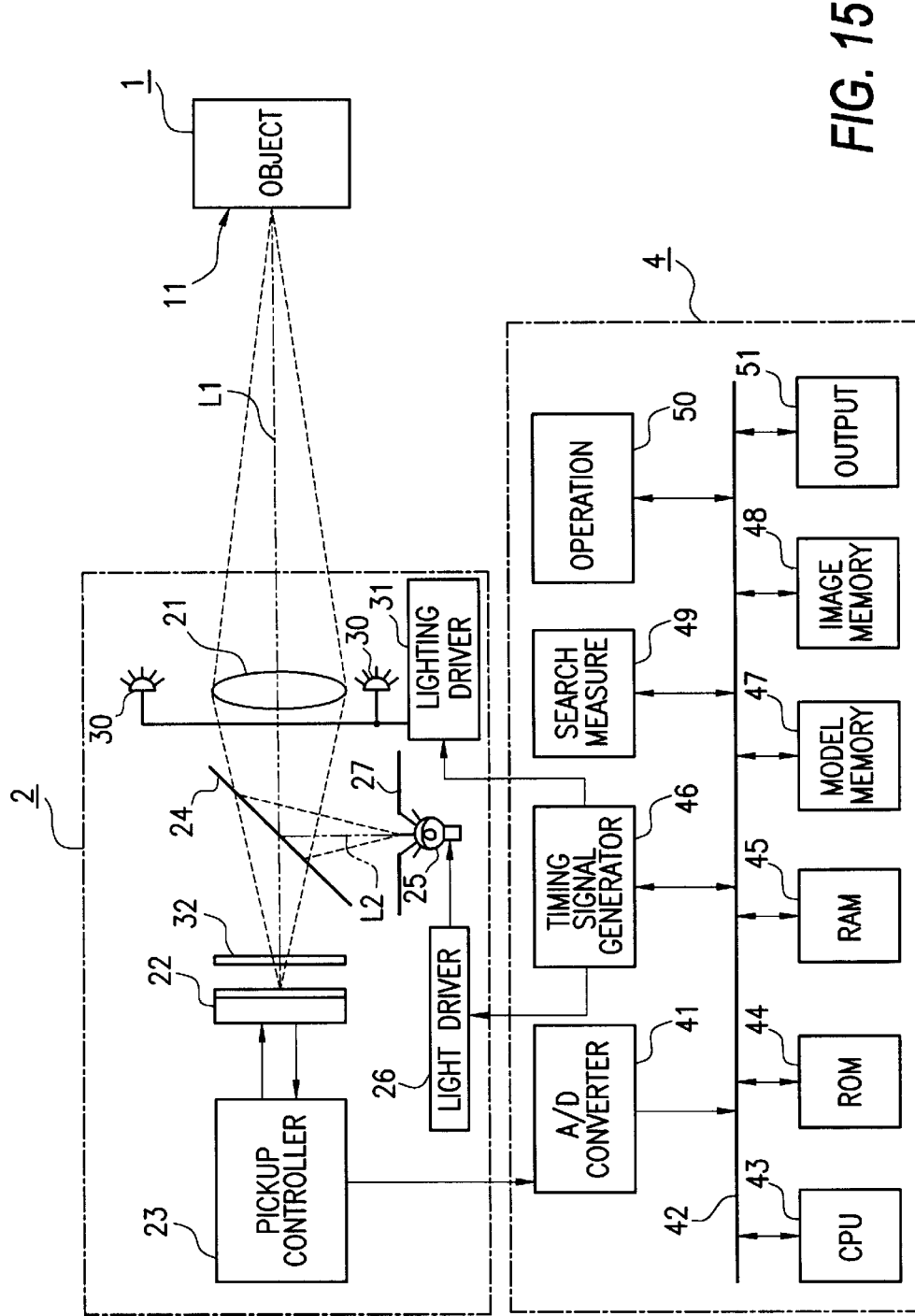
FIG. 15 is a block diagram of an image pickup device and an image processing device as a fourth embodiment of this invention.

In FIG. 15 there is shown a block diagram of an image pickup device 2 and an image processing device 4 as a fourth embodiment of this invention, in which the same reference numbers are given to the components corresponding to those of the third embodiment (shown in FIG. 12) and their detailed explanation is omitted In this embodiment, there is employed the same construction as that of FIG. 12 except such a construction in which an optical filter 32 transmitting only the signal having the same frequency as the illumination frequency of the illumination light sources 30 is disposed in front of the image pickup element 22.

In this embodiment, the optical filter 32 transmits only the luminescence frequency signal of the light sources 30 and intercepts the luminescence frequency signal of the projection light source 25, whereby any shifting control such as shifting the projection timing of the source 25 from the light receive timing of the element 22 (as shown in FIGS. 9 and 10) is not needed, and the inspection and measurement can be performed with the projection light source 25 always indicating an inspection region.

(Fifth Embodiment)

Figure 16:
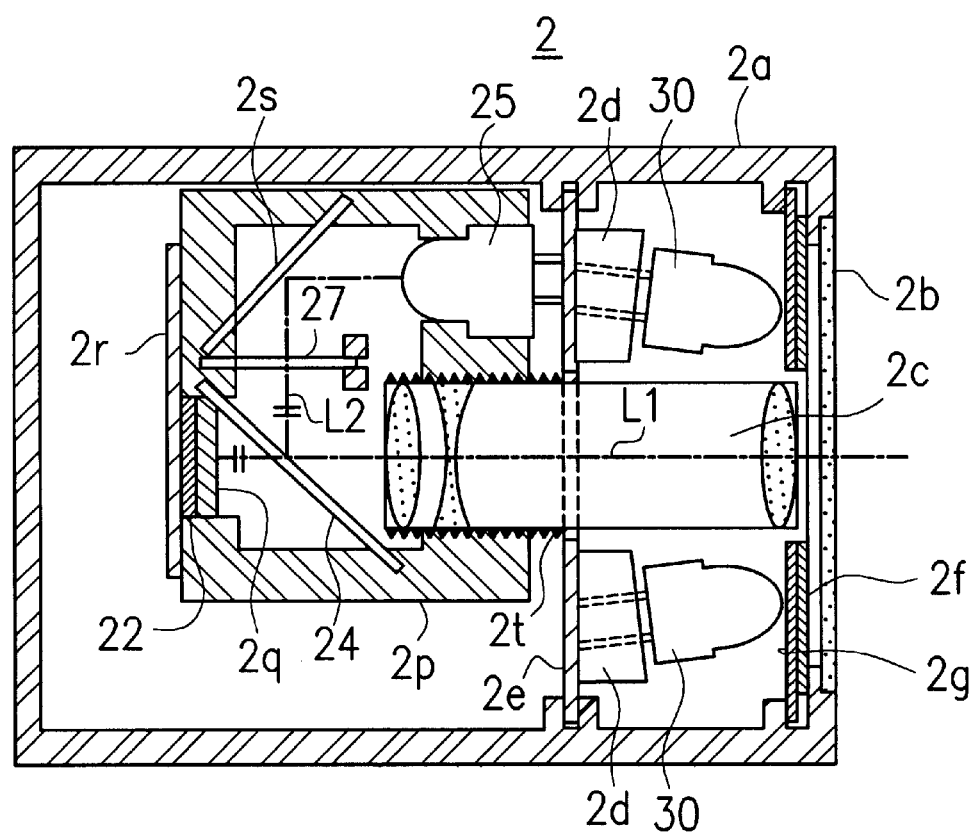
FIG. 16 is a schematic sectional side view of an image pickup device as a fifth embodiment of this invention.

FIG. 16 is a schematic sectional side view of an image pickup device to show a concrete mounting frame example as a fifth embodiment of this invention, in which the same reference numbers are given to the contents corresponding to those of the third embodiment (shown in FIG. 12) and their detailed explanation is omitted. An image pickup device 2 has a sealed housing of a rectangular or cylindrical configuration in which an opening of the C-shaped housing 2a is fixed by a transparent plate 2b. Inside of the transparent panel 2b there is mounted a cylindrical lens unit 2c which encloses in a depth direction a combination lens corresponding to the lens 21 of FIG. 12.

A plurality of illumination light sources 30 are fixed on a printed circuit board 2e through spacers 2d. The light sources 30 are mounted slanting slightly inwardly by the spacers 2d to illuminate the measured surface 11 of the object 1.

A polarizing filter 2f and a M (micro lens array) 2g are mounted in a laminated fashion and in front of the light sources 30 on the inner side of the transparent plate 2b. The MLA 2g is composed of a large number of micro lenses formed on a flat plane and employed to uniformly direct light projected from the sources 30 for uniform brilliance on a flat plane to provide uniform lighting. If desired, the transparent plate 2b and the MLA 2g may be molded as a single unit.

An optical holder 2p is mounted behind the printed circuit board 2e and houses a rear half portion of the lens unit 2c therein. Behind the lens unit 2c there are mounted a half mirror 24 and a picture pickup element 22 on an optical axis L1. A polarizing filter 2q is mounted on a front wall of the pickup element 22, and a printed circuit board 2r mounted on a rear of the optical holder 2p is mounted on a rear wall of the element 22. On the board 2r there are mounted electronic components (not shown) to provide a peripheral circuit of the image pickup element 22.

Polarization directions of the polarizing filters 2q and 2f are crossed with respect to each other to avoid entry of light from the illumination light source 30 into the pickup element 22. The polarizing filter 2q is interposed between the half mirror 24 and the image pickup element 22 without being arranged within a path projected by the projection light source 25 through the lens unit 2c to avoid reduction of light quantity of the projection.

A slit plate 27 is mounted on the optical axis L2 in a reflection direction of the half mirror 24 by the same distance as that to the pickup element 22, and a mirror 2s is disposed behind the plate 27. The projection light source 25 is disposed in the reflection direction of the mirror 2s. The half mirror 24 and the mirror 2s are respectively placed at a slant angle of 45 degrees on the optical axes L1 and L2, so that the projection light source 25 is mounted in parallel with the optical axis L1 behind the printed circuit board 2e.

The lens unit 2c is disposed for a forward and back movement by mounting the lens unit 2c to the optical holder 2p through a screw 2t for a screw engagement.

(Sixth Embodiment)

Figure 17:
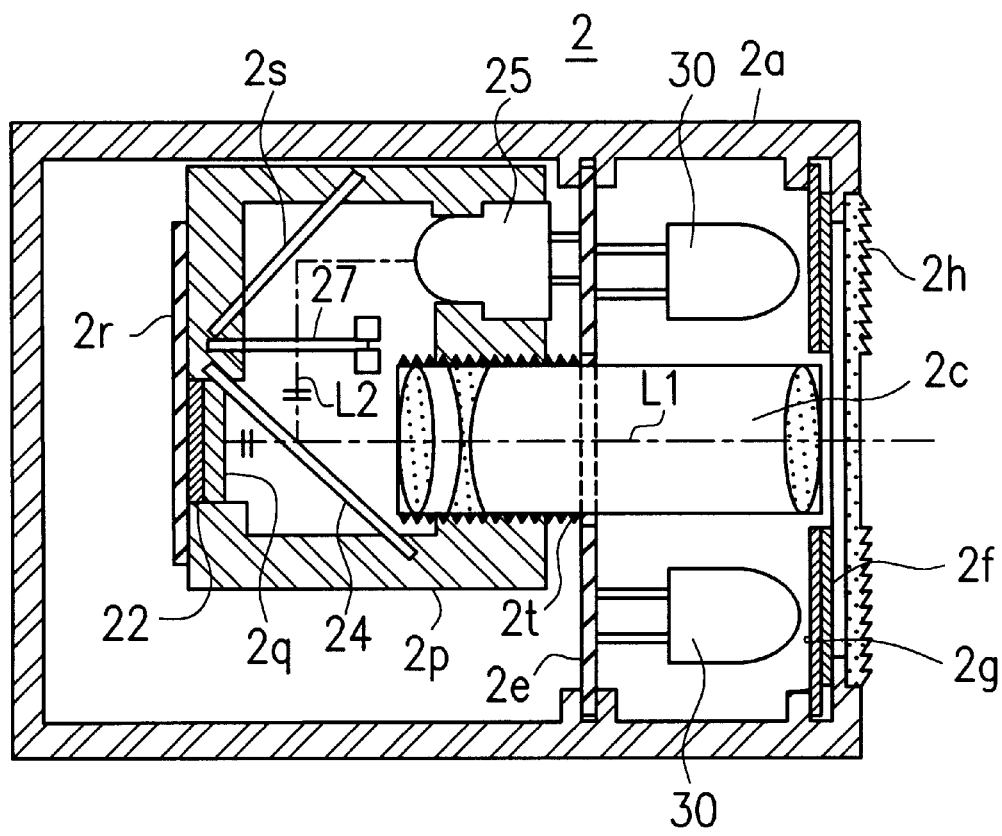
FIG. 17 is a schematic sectional side view of an image pickup device as a sixth embodiment of this invention.

FIG. 17 is a schematic sectional side view of an image pickup device to show a concrete mounting frame example as a sixth embodiment of this invention, in which the same reference numbers are given to the components corresponding to those of the fifth embodiment (shown in FIG. 16) and their detailed explanation is omitted.

An image pickup device 2 of this embodiment has the same construction as that of the fifth embodiment shown in FIG. 16, except such a construction that a transparent prism array 2h is disposed instead of the transparent plate 2b and a plurality of illumination light sources 30 are directly mounted on a printed circuit board 2e without employing the spacer 2d.

The prism array 2h is composed of a large number of micro prisms formed in one plane opposed to the light sources 30 so as to a little inwardly refract light projected from the light sources 30 to the measurement surface 11 of the object 1. Accordingly, the light sources may be normally mounted to stand erect on the board 2e.

(Seventh Embodiment)

Figure 18:
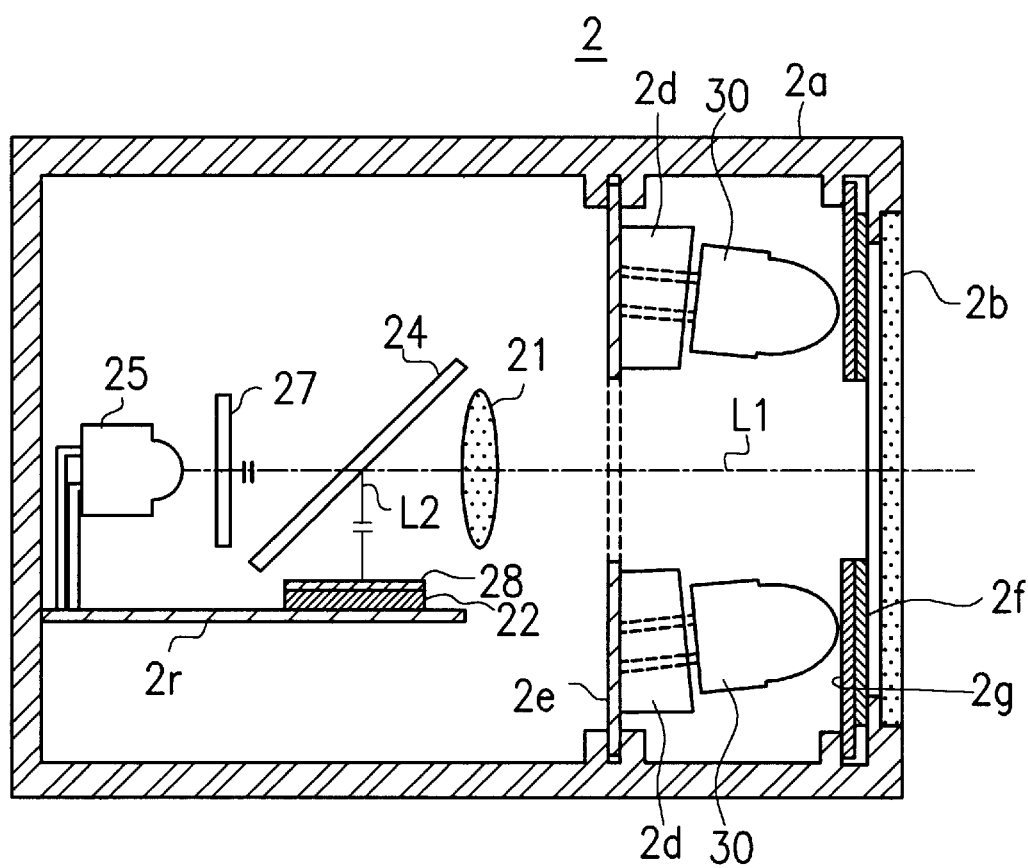
FIG. 18 is a schematic sectional side view of an image pickup device as a seventh embodiment of this invention.
Figure 19:
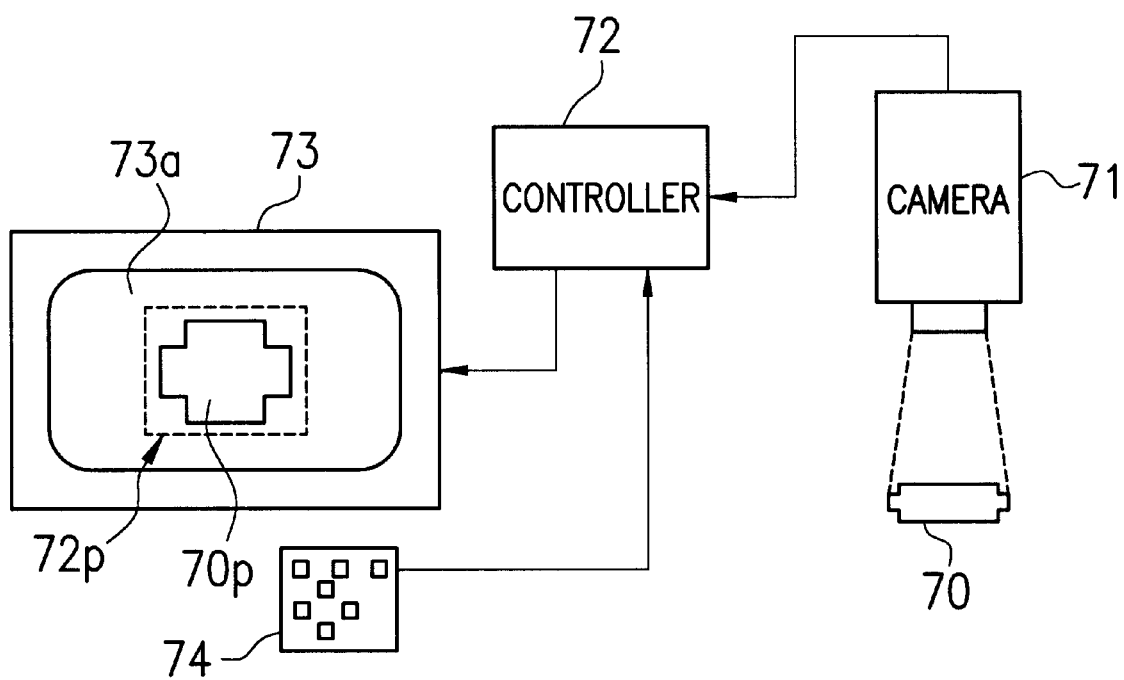
FIG. 19 is a block diagram of a conventional image inspection device.

FIG. 18 is a schematic sectional side view of an image pickup device to show a concrete mounting frame example as a seventh embodiment of this invention, in which the same reference numbers are given to the components corresponding to those of the fifth embodiment (shown in FIG. 16) and their detailed explanation is omitted.

An image pickup device 2 of this embodiment includes lenses 21, a half mirror 24, a slit plate 27 and a projection light source 25 on an optical axis L1 which are disposed inside the transparent plate 2b. fixed on an opening of a C-shaped housing 2a.

A plurality of illumination light sources 30 are mounted on a printed circuit board 2e through spacers 2d at the periphery of the lens 21. The sources 30 are mounted slanting little inwardly by the spacers 2d to project light to the measurement surface 11 of the object. A polarizing filter 2f and a MLA 2g are laminated and placed in front of each light source 30.

On an optical axis L2 in a reflection direction of the half mirror 24, there is mounted an image pickup element 22 which is placed by spacing at the same remote distance from the mirror 24 as that of the slit plate 27. A polarizing filter 28 is mounted in front of the element 22 to cross the polarization direction of the polarizing filters 2f, and a printed circuit board 2r is horizontally disposed at the back of the element. On the board 2r there are mounted electronic components (not shown in drawings) and the projection light source 25.

By thus disposing the pickup element 22 in the reflection direction, distortion of the image is improved in comparison with mounting the element in the transferring direction because distortion of the image appears by difference of incident angles to the mirror 24.

What is claimed is:

1. An image pickup device for providing a model image and an input image in combination with an image processing device which registers said model image and conducts a matching process by searching for an image which agrees with said registered model image within a measurement region included in said input image, where in the improvement comprises:

projecting means in said image pickup device for directly projecting a registration region designating image and a measurement region designating image onto an object for showing a registration region of which image is registered as said model image and said measurement region to an operator.

2. An image pickup device according to claim 1, wherein said projecting means projects said region designating image at a timing different from a light receiving timing of said image pickup means.

3. An image pickup device according to claim 1, wherein said projecting means projects said region designating image having a predetermined color, and said image pickup device has an optical filter or a dichroic mirror in the light receiving path to prevent receipt of light having said predetermined color.

4. An image pickup device according to claim 1, further comprising:

illumination means disposed around said lens for illuminating said object.

5. An image pickup device according to claim 4, wherein said projecting means projects said region designating image at a timing different from a light receiving timing of said image pickup means, and said illumination means illuminates said object at a synchronous timing with said light receiving timing of said image pickup means.

6. An image pickup device according to claim 4, wherein said projecting means projects said region designating image having a first color, said illumination means illuminates said object with light having a second color, and said image pickup device has an optical filter or a dichroic mirror in the light receiving path to prevent receipt of light having the first color and to permit receipt of light having the second color.

7. The image pickup device according to claim 1, wherein said projecting means projects said registration region designating image and said measurement region designating image simultaneously.

8. An imaging device comprising:

an image processing device;

an image pickup device for providing a model image and an input image of an object to said image processing device, said image processing device registering said model image;

a projection light source; and a slit plate disposed between said projection light source and said object, said slit plate and said projection light source cooperating to directly project a registration region designating image and a measurement region designating image onto said object, said registration region designating image showing a registration region of said registered model image, wherein said image processing device conducts a matching process by searching for an image which agrees with said registered model image within said measurement region in said input image.

9. An imaging device according to claim 8, wherein said projection light source and slit plate cooperate to project said region designating image at a timing different from a light receiving timing of said image pickup device.

10. An imaging device according to claim 8, wherein said region designating image has a predetermined color, and said image pickup device has an optical filter or a dichroic mirror in a light receiving path to prevent receipt of light having said predetermined color.

11. An imaging device according to claim 8, wherein said image pickup device further comprises:

a lens through which said input image is focused; and a plurality of light sources disposed around said lens, said plurality of light sources illuminating said object.

12. The imaging device according to claim 11, wherein said plurality of light sources are light emitting diodes.

13. An imaging device according to claim 11, wherein said projection light source and slit plate cooperate to project said region designating image at a timing different from a light receiving timing of said image pickup device, and said plurality of light sources illuminate said object at a synchronous timing with said light receiving timing of said image pickup device.

14. An imagiing device according to claim 11, wherein said region designating image has a first color, and said plurality of light sources illuminate said object in a second color, and said image pickup device has an optical filter or a dichroic mirror in a light receiving path to prevent receipt of light having said first color and to permit receipt of light having said second color.

15. The imaging device according to claim 8, wherein said light source and slit plate cooperate to project said registration region designating image and said measurement region designating image simultaneously.

* * * * *